US010426372B2

(12) United States Patent
Yu et al.

(10) Patent No.: US 10,426,372 B2
(45) Date of Patent: Oct. 1, 2019

(54) IMAGE REGISTRATION SYSTEM WITH NON-RIGID REGISTRATION AND METHOD OF OPERATION THEREOF

(71) Applicant: Sony Corporation, Tokyo (JP)

(72) Inventors: Liangyin Yu, Fremont, CA (US); Ming-Chang Liu, San Jose, CA (US)

(73) Assignee: Sony Corporation, Tokyo (JP)

( * ) Notice: Subject to any disclaimer, the term of this patent is extended or adjusted under 35 U.S.C. 154(b) by 371 days.

(21) Appl. No.: 14/339,352

(22) Filed: Jul. 23, 2014

(65) Prior Publication Data

US 2016/0027178 A1 Jan. 28, 2016

(51) Int. Cl.
*A61B 5/055* (2006.01)
*A61B 6/03* (2006.01)
(Continued)

(52) U.S. Cl.
CPC .............. *A61B 5/055* (2013.01); *A61B 6/032* (2013.01); *A61B 6/037* (2013.01); *A61B 6/463* (2013.01);
(Continued)

(58) Field of Classification Search
CPC ........... A61B 5/05; A61B 6/463; A61B 6/032; A61B 6/037; A61B 5/055; A61B 6/5235;
(Continued)

(56) References Cited

U.S. PATENT DOCUMENTS

| 8,693,730 B2 * | 4/2014 | Umasuthan | A61B 1/00149 382/103 |
| 2005/0148859 A1 * | 7/2005 | Miga | G06K 9/00214 600/410 |

(Continued)

FOREIGN PATENT DOCUMENTS

| EP | 2525323 A1 | 11/2012 | |
| WO | WO 201316321 A1 * | 10/2013 | A61B 5/14553 |

OTHER PUBLICATIONS

Fabry et al., "3D non-rigid point cloud based surface registration based on mean shift". WSCG 2010. pp. 121-128 (Year: 2010).*

*Primary Examiner* — James M Kish
(74) *Attorney, Agent, or Firm* — Haverstock & Owens LLP

(57) ABSTRACT

An image registration system, and a method of operation of an image registration system thereof, including: an imaging unit for obtaining a pre-operation non-invasive imaging volume and for obtaining an intra-operation non-invasive imaging volume; and a processing unit including: a rigid registration module for generating a rigid registered volume based on the pre-operation non-invasive imaging volume, a region of interest module for isolating a region of interest from the intra-operation non-invasive imaging volume, a point generation module, coupled to the region of interest module, for determining feature points of the region of interest, an optimization module, coupled to the point generation module, for matching the feature points with corresponding points of the rigid registered volume for generating a matched point cloud, and an interpolation module, coupled to the optimization module, for generating a non-rigid registered volume based on the matched point cloud for display on a display interface.

18 Claims, 9 Drawing Sheets

(51) Int. Cl.
*A61B 6/00* (2006.01)
*G06T 7/00* (2017.01)
*G06T 7/33* (2017.01)

(52) U.S. Cl.
CPC .......... *A61B 6/5235* (2013.01); *G06T 7/0012* (2013.01); *G06T 7/33* (2017.01); *A61B 6/5247* (2013.01); *G06T 2200/04* (2013.01); *G06T 2207/10072* (2013.01); *G06T 2207/30004* (2013.01); *G06T 2207/30016* (2013.01); *G06T 2219/2004* (2013.01)

(58) Field of Classification Search
CPC ....... A61B 6/5247; G06T 7/0028; G06T 7/33; G06T 7/0012; G06T 2207/30016; G06T 2207/10072; G06T 2207/30004; G06T 2219/2004

See application file for complete search history.

(56) References Cited

U.S. PATENT DOCUMENTS

| | | | |
|---|---|---|---|
| 2005/0228251 A1* | 10/2005 | Grabb | A61B 5/7445 600/407 |
| 2009/0041314 A1* | 2/2009 | Vercauteren | G02B 21/367 382/128 |
| 2009/0118640 A1* | 5/2009 | Miller | A61B 90/36 600/567 |
| 2010/0001996 A1 | 1/2010 | Shen et al. | |
| 2012/0015316 A1* | 1/2012 | Sachdeva | G06T 17/00 433/24 |
| 2012/0114223 A1* | 5/2012 | Luisi | G06T 7/0014 382/154 |
| 2014/0003700 A1* | 1/2014 | Hermosillo Valadez | G06T 11/003 382/131 |
| 2014/0037161 A1* | 2/2014 | Rucker | G06T 7/30 382/128 |
| 2014/0073907 A1* | 3/2014 | Kumar | A61B 10/00 600/414 |
| 2014/0193053 A1* | 7/2014 | Kadoury | G06T 11/008 382/131 |
| 2014/0226895 A1* | 8/2014 | Babin | G06K 9/00214 382/154 |
| 2015/0078642 A1* | 3/2015 | Fang | A61B 5/14553 382/131 |
| 2015/0324998 A1* | 11/2015 | Song | G06T 3/40 382/171 |

\* cited by examiner

IMAGE REGISTRATION SYSTEM WITH NON-RIGID REGISTRATION AND METHOD OF OPERATION THEREOF

TECHNICAL FIELD

The present invention relates generally to an image registration system, and more particularly to a system for non-rigid registration of images.

BACKGROUND ART

Advances in medical technology have improved recovery times and reduced complication rates. One significant advance is image-guided surgery (IGS), which uses various imaging techniques to help plan and execute surgeries. The imaging techniques can include CT scans or MRI scans. The scans can help a surgeon create a good surgery plan to minimize the risks inherent in any surgery. The ability for a surgeon to easily mitigate those risks is paramount to the success of the surgery.

However, because of the inherently pliable nature of human organs and structures, it is sometimes necessary to image the area of interest more than once in order to ensure that a location of interest has not moved from its expected location due to deformation of human tissue or movement of organs. This presents a problem in that generating a full set of images usable in image-guided surgery can take an inordinate amount of time in the middle of surgery while a patient is vulnerable to injury or infection.

Thus, a need still remains for a better way of generating usable images. In view of the ever-growing importance of healthcare, it is increasingly critical that answers be found to these problems. Growing consumer expectations and the diminishing opportunities for meaningful product differentiation in the marketplace make it critical that answers be found for these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

The present invention provides a method of operation of an image registration system that includes obtaining a pre-operation non-invasive imaging volume with an imaging unit; generating a rigid registered volume based on the pre-operation non-invasive imaging volume; obtaining an intra-operation non-invasive imaging volume with the imaging unit; isolating a region of interest from the intra-operation non-invasive imaging volume; determining feature points of the region of interest; matching the feature points with corresponding points of the rigid registered volume for generating a matched point cloud; and generating a non-rigid registered volume based on the matched point cloud for display on a display interface.

The present invention provides an image registration system that includes an imaging unit for obtaining a pre-operation non-invasive imaging volume and for obtaining an intra-operation non-invasive imaging volume; and a processing unit including: a rigid registration module for generating a rigid registered volume based on the pre-operation non-invasive imaging volume, a region of interest module for isolating a region of interest from the intra-operation non-invasive imaging volume, a point generation module, coupled to the region of interest module, for determining feature points of the region of interest, an optimization module, coupled to the point generation module, for matching the feature points with corresponding points of the rigid registered volume for generating a matched point cloud, and an interpolation module, coupled to the optimization module, for generating a non-rigid registered volume based on the matched point cloud for display on a display interface.

Certain embodiments of the invention have other steps or elements in addition to or in place of those mentioned above. The steps or element will become apparent to those skilled in the art from a reading of the following detailed description when taken with reference to the accompanying drawings.

BEST MODE FOR CARRYING OUT THE INVENTION

Figure 1:
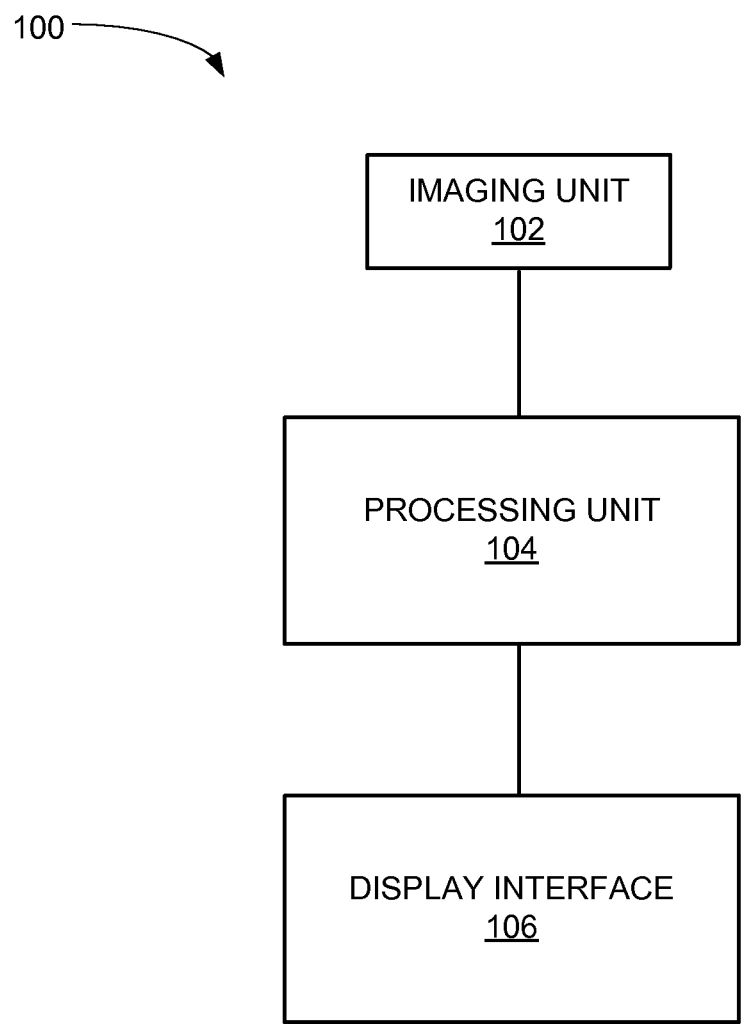
FIG. 1 is a schematic of an image registration system in a first embodiment of the present invention.

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known circuits, system configurations, and process steps are not disclosed in detail.

The drawings showing embodiments of the system are semi-diagrammatic and not to scale and, particularly, some of the dimensions are for the clarity of presentation and are shown exaggerated in the drawing FIGs. Similarly, although the views in the drawings for ease of description generally show similar orientations, this depiction in the FIGs. is arbitrary for the most part. Generally, the invention can be operated in any orientation.

The same numbers are used in all the drawing FIGs. to relate to the same elements. The embodiments have been numbered first embodiment, second embodiment, etc. as a matter of descriptive convenience and are not intended to have any other significance or provide limitations for the present invention.

For expository purposes, the term "horizontal" as used herein is defined as a plane parallel to the plane of the bottom of the display interface, regardless of its orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane, as shown in the figures.

Referring now to FIG. 1, therein is shown a schematic of an image registration system 100 in a first embodiment of the present invention. Shown are an imaging unit 102, a processing unit 104, and a display interface 106.

The imaging unit 102 can be a hardware unit capable of capturing images of biological structures. The imaging unit 102 is connected to the processing unit 104, which is connected to the display interface 106. The display interface 106 can display images from the imaging unit 102 after processing by the processing unit 104. Images captured by the imaging unit 102 and processed by the processing unit 104 to be understandable on viewing can be said to be registered images, for example.

The processing unit 104 can be any of a variety of semiconductor devices such as a general purpose computer, a specialized device, embedded system, or simply a computer chip integrated with the imaging unit 102 and/or the display interface 106. The display interface 106 can utilize a variety of display technologies such as LCD, LED-LCD, plasma, holographic, OLED, front and rear projection, CRT, or other display technologies.

The processing unit 104 can contain many modules capable of performing various functions. For example, the processing unit 104 can have an image block module coupled to an automatic blood detection module containing a red color dominance module, a red color deviation module, a red color colorfulness module, and a threshold module, a masking module coupled to the automatic blood detection module, and an overlay module coupled to the masking module. The processing unit 104 can run some or all of the modules simultaneously.

For example, the imaging unit 102 can be used in order to capture images from within a patient with which to create a surgery plan for image-guided surgery. The imaging unit 102 can be used from the outside of a patient, with the display interface 106 showing a resulting image after processing by the processing unit 104. The resulting (registered) image can be used to determine how to safely perform surgery in delicate areas such as the brain. Image-guided surgery is given as an example of how the image registration system 100 can be used, but it is understood that the image registration system 100 can be used in different contexts. For example, the image registration system 100 can be integrated into a portable MRI, CT, or PET scanner, phone, or tablet, or operated as a scanner attached to a personal computer or laptop.

Figure 2:
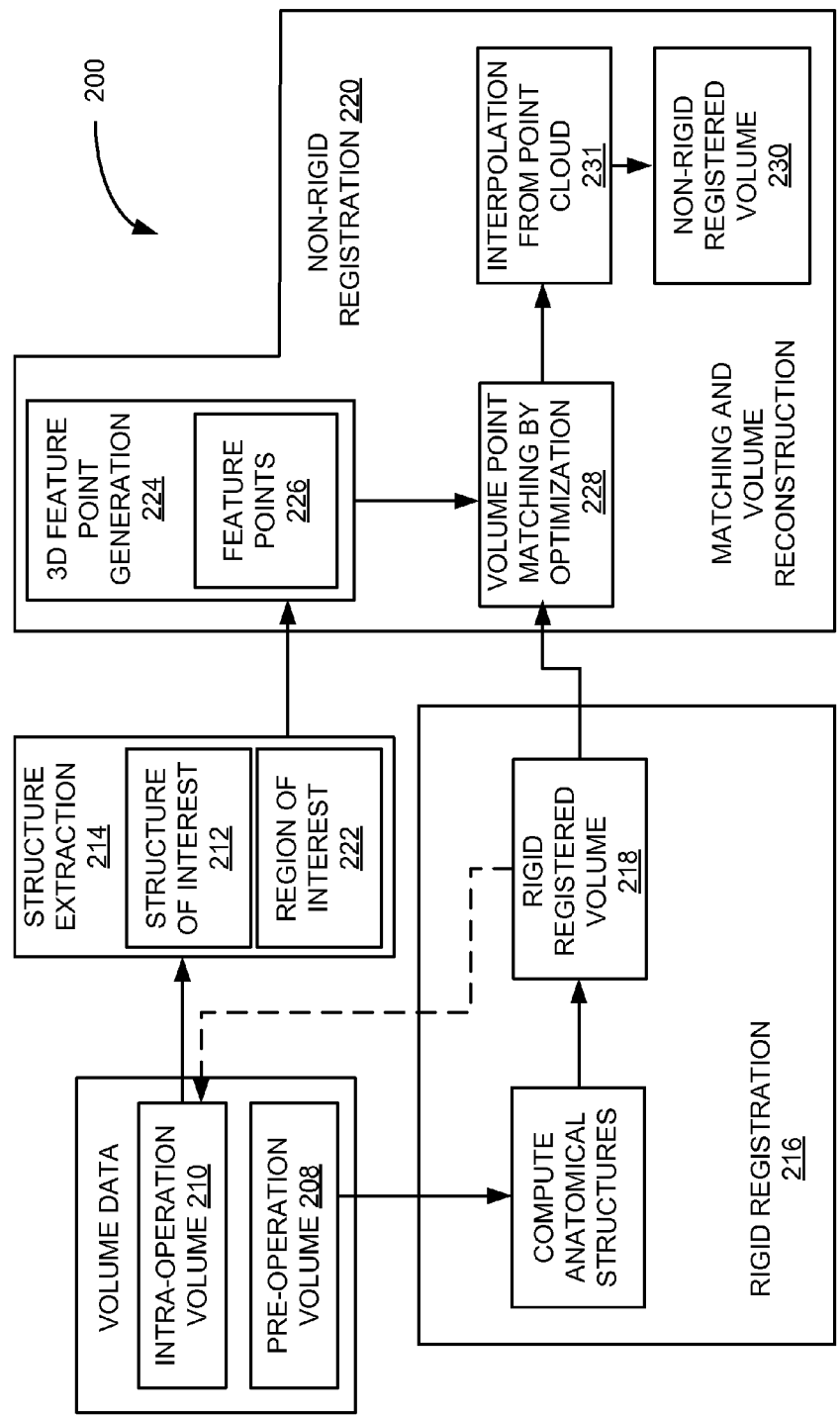
FIG. 2 is a system diagram of the image registration system in a second embodiment of the present invention.

Referring now to FIG. 2, therein is shown a system diagram of the image registration system 200 in a second embodiment of the present invention. In this embodiment, magnetic resonance imaging (MRI) data from a scan of a patient's head is used, but it is understood that scan data through various techniques and from any part of the body can have the invention applied to it. In image-guided surgery it is often necessary to take a scan during surgery. Information from a MRI, computed tomography (CT), and/or positron emission tomography (PET) scan, for example, taken with the imaging unit 102 of FIG. 1 before the surgery for planning can be considered a pre-operation non-invasive imaging volume 208. Information from a MRI, CT, and/or PET scan taken during surgery for further planning or adjustment of a plan can be considered an intra-operation non-invasive imaging volume 210. The pre-operation non-invasive imaging volume 208 and the intra-operation non-invasive imaging volume 210 are image information taken using non-invasive techniques such as magnetic resonance imaging (MRI), functional MRI (fMRI), magnetic resonance angiogram (MRA), diffusion tensor imaging (DTI), computed axial tomography (CT, or CAT), and positron emission tomography (PET).

The type of scan used can be tailored to the type of image-guided surgery being performed. For example, because MRI scans are more effective at imaging soft tissues in organs such as the brain, brain surgery may be served well by the pre-operation non-invasive imaging volume 208 and the intra-operation non-invasive imaging volume 210 being some combination of magnetic resonance imaging scans.

The intra-operation non-invasive imaging volume 210 can be acted on by the structure extraction module which can determine the boundaries of the brain and extract the parts of the intra-operation non-invasive imaging volume 210 which correspond to the brain, for example. In other words, in this example of a patient's head, other anatomical structures such as the face and skull are removed to form a structure of interest 212 in a structure extraction step 214. This step can use anatomical structures determined in a rigid registration step 216 as a reference guide to speed up the process of the structure extraction step 214. Because magnetic resonance imaging (MRI) can only scan in two dimensions, these examples of the intra-operation non-invasive imaging volume 210 and the pre-operation non-invasive imaging volume 208 are a combination of many MRI slices aligned to form a three-dimensional volume. There are different types of MRI scanning techniques, and one or more can be combined to obtain the intra-operation non-invasive imaging volume 210, for example. In this example, the structure of interest 212 is the brain, but it is understood that the structure of interest 212 can be any structure or part of a structure of the organism being scanned.

In the rigid registration step 216, the pre-operation non-invasive imaging volume 208 can be used by the rigid registration module to determine the boundaries of the anatomical structures and then to generate a rigid registered volume 218. The rigid registered volume 218 generation process is described in greater detail in the next figure.

The rigid registered volume 218 can be used to initialize a non-rigid registration step 220. The non-rigid registration step 220 is for generating a map much like the rigid registered volume 218, but also taking into account the pliable and deformable (non-rigid) nature of the human body, so that even as anatomical structures shift due to disease or the surgery itself, locations of interest (such as a tumor location, for example) in image-guided surgery continue to be represented accurately. The rigid registered volume 218 can also be used in the generation of the intra-operation volume 210, for example. The dotted line connecting the rigid registered volume 218 and the intra-operation volume 210 represents the possibility of using the rigid registered volume 218 in multiple parts of the non-rigid registration step 220.

A region of interest 222 can be extracted from the structure of interest 212, with the location and features of the region of interest 222 determined by surgical necessity, using the region of interest module, for example. The region of interest 222 can be the same as the structure of interest 212 or smaller than the structure of interest 212 depending on the need for accuracy in particular regions. The region of interest 222 can undergo a three-dimensional feature point generation step 224 using the point generation module which can generate feature points 226 marking features of interest. For example, each of the feature points 226 can be at a distinctive feature of the region of interest 222 such as inflection points, ridges, folds, or any discernable feature of the region of interest 222.

Using the rigid registered volume 218 as a reference or a map of anatomical structures, the feature points 226 of the region of interest 222 can then be matched through the optimization module in an optimization step 228 to corresponding points of the rigid registered volume 218. One example approach is to coarsely match distinctive anatomical structures with easily discerned features of the region of interest 222 followed by determining a maximum displacement distance that it is expected any given feature could move, and restrict the search for corresponding points to within a space around the feature points 226 defined by the maximum displacement distance. The feature points 226 used for the optimization step 228 can be considered to be part of a point cloud, or a specific collection of the feature points 226. The optimization step 228 can be done in various ways, but one example is presented below where the region of interest 222 is noted with xk, and it is matched to another region yk. The optimization step 228 is done, for example, using Equation 1. The equation is for example only, and it is understood that other methods of matching the feature points 226 are possible.

$$\min \sum_{k=1}^{N} \|M(y_k, \phi(x_k))\| + \lambda \int_D \|S(\phi(x))\| dx \qquad \text{Equation 1}$$

It has been discovered that using the rigid registered volume 218 as a reference guide for initialization of the non-rigid registration step 220 speeds up initialization and improves accuracy within the region of interest 222. Because the pre-operation non-invasive imaging volume 208 and the intra-operation non-invasive imaging volume 210 are of the same patient, taken from the same location, coarse alignment of major features is very quick. It is understood that a particular feature in non-rigid registration must be somewhat close to the corresponding feature in rigid registration, as anatomical structures can only realistically move a small distance in spite of the deformable characteristics of organs and other biological structures. This leads to a smaller search space for matching the feature points 226, which leads to faster processing as compared to searching an entire imaging volume.

Further, regarding the example of Equation 1, a simpler equation than traditional methods is possible because of the use of the region of interest 222 and the rigid registered volume 218 as a reference. The reference map allows for easy and quick alignment of large features which reduce the search space and mathematical complexity of a search function. Traditional techniques which optimize the entire volume are computationally expensive and slow to converge on a solution. It has been discovered that as compared to traditional techniques, the use of the rigid registered volume 218 as a reference map and the region of interest 222 to shrink the search space, along with a simpler search equation such as Equation 1, allows for a 10-fold or greater reduction in time to converge on a solution. Because non-rigid registration is necessary in the middle of image-guided surgery, faster convergence on a solution so that a good internal view can be generated even after deformation has taken place will lead to less time taken during surgery, less time with the patient vulnerable, fewer chances of complications, and better surgical outcomes.

The matched point cloud can be used as a starting point for reconstructing the rest of the structure of interest 212 or for generating a non-rigid registered volume 230. The non-rigid registered volume 230 can have all of the internal and external features of the intra-operation non-invasive imaging volume 210, but in a usable form that is not a simple collection of images; the non-rigid registered volume 230 can be manipulated in three-dimensions, and can contain deformation information. In order to save on processing time, rather than directly registering the image, the point cloud can be used for example, as an input to a meshless interpolation kernel such as a radial basis function to reconstruct volume data and get a full picture of the region of interest 222 or the structure of interest 212. This can be done through an interpolation step 231 using the interpolation module, for example.

The benefit of using a radial basis function is that no grid points are necessary, and increasing accuracy of results only requires an increase in the number of the feature points 226 that are used. The number and local density of the feature points 226 used can be modified depending on the requirements of the image-guided surgery, with fewer of the feature points 226 where detail is less important, and a higher density of the feature points 226 chosen and used where detail is more important, for example. It has also been found that internal and external structures can be accurately recreated using the interpolation module acting only on the feature points 226 in the matched point cloud.

Figure 3:
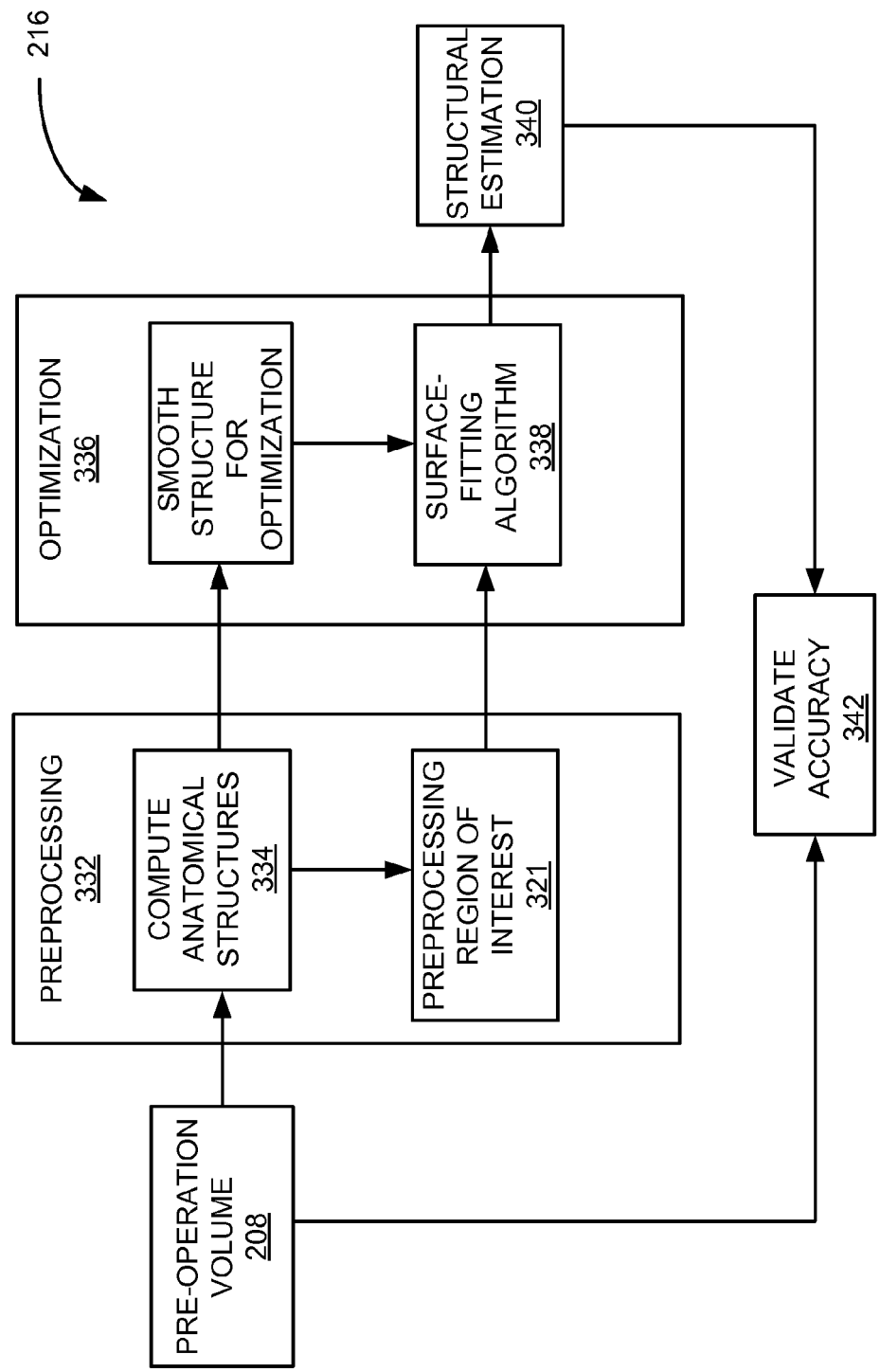
FIG. 3 is a detailed flow chart of the rigid registration step of FIG. 2.

Referring now to FIG. 3, therein is shown a detailed flow chart of the rigid registration step 216. In a pre-processing step 332, the pre-operation non-invasive imaging volume 208 first has anatomical structures detected and isolated in an anatomical structure computation step 334 using an anatomical structure module, for example. The pre-operation non-invasive imaging volume 208 can be composed of various combinations of MRI or CT scan data, for example. For example, the pre-operation non-invasive imaging volume 208 can be a fusion of MRI data from multiple modalities of MRI scans. This means many different types of rigid registration are possible such as MRI T1-T1 registration, MRI T1-T2 registration, CT-MRI registration, MRI-DTI registration, and MRI-fMRI registration, for example. The pre-operation non-invasive imaging volume 208 can be compared to a reference image or set of images in order to more quickly isolate anatomical structures, for example. The type of registration chosen can reflect the types of structures of greatest interest during image-guided surgery, for example.

A pre-processing region of interest 321, which may or may not be the same as the region of interest 222 of FIG. 2 used in non-rigid registration, can be manually or automatically selected from the anatomical structures. The pre-processing region of interest 321 is chosen in order to increase accuracy in the pre-processing region of interest 321. It has been found that doing rigid registration on all portions of the pre-operation non-invasive imaging volume 208 will decrease accuracy. The size and location of the pre-processing region of interest 321 can be chosen based on surgical necessity.

In a rigid optimization step 336, the anatomical structures are smoothed, or sharpened, in order to ensure that boundaries between different anatomical structures are clear. The smoothed anatomical structures within the pre-processing region of interest 321 are run through a surface-fitting algorithm 338 in order to transform the image into a three-dimensional model with clearly delineated boundaries between anatomical structures. For example, the surface-fitting algorithm 338 can be a Levenberg-Marquardt algorithm, but it is understood that other surface-fitting algorithms can be used.

The output is a structural estimation 340 of the anatomical structures found in the pre-processing step 332, and it undergoes an accuracy validation step 342. In the accuracy validation step 342, the structural estimation 340 is compared to the original information in the pre-operation non-invasive imaging volume 208 using a validation module, for example. Once the accuracy of rigid registration has been validated, the rigid registered volume 218 of FIG. 2 can be complete.

Figure 4:
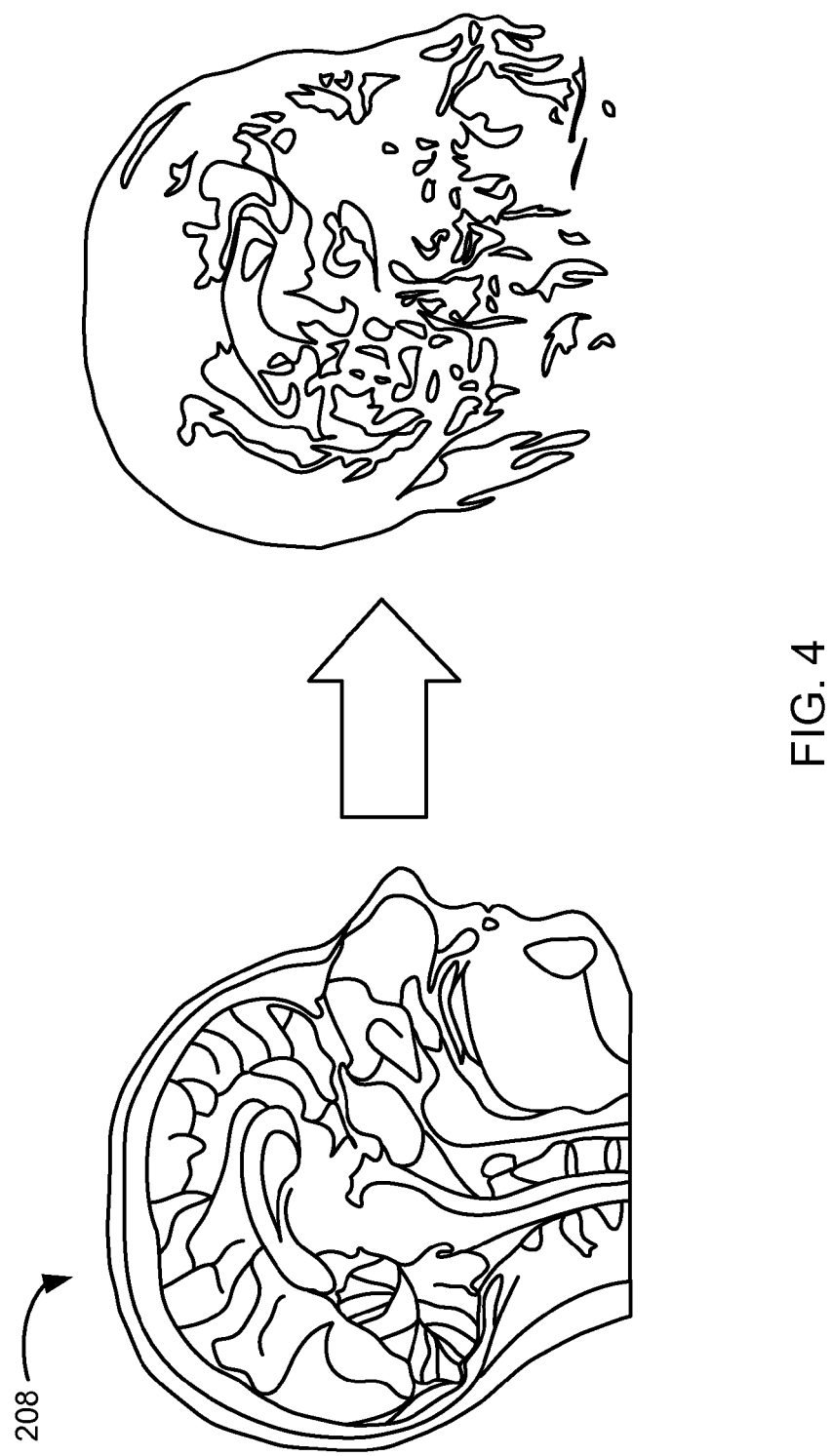
FIG. 4 is an example of the anatomical structure computation step of FIG. 3 in a preprocessing phase of operation.

Referring now to FIG. 4, therein is shown an example of the anatomical structure computation step 334 of FIG. 3 in a preprocessing phase of operation. The pre-operation non-invasive imaging volume 208 can be seen on the left side. Due to the limitations of line drawings, the pre-operation non-invasive imaging volume 208 is shown in two dimensions for clarity, although it is understood that the pre-operation non-invasive imaging volume 208 can have three dimensions. After some computation, the anatomical structures can be seen on the right side of the figure. It is understood that the anatomical structures shown are for example only, and that different methods of isolating anatomical structures can lead to different outcomes.

Figure 5:
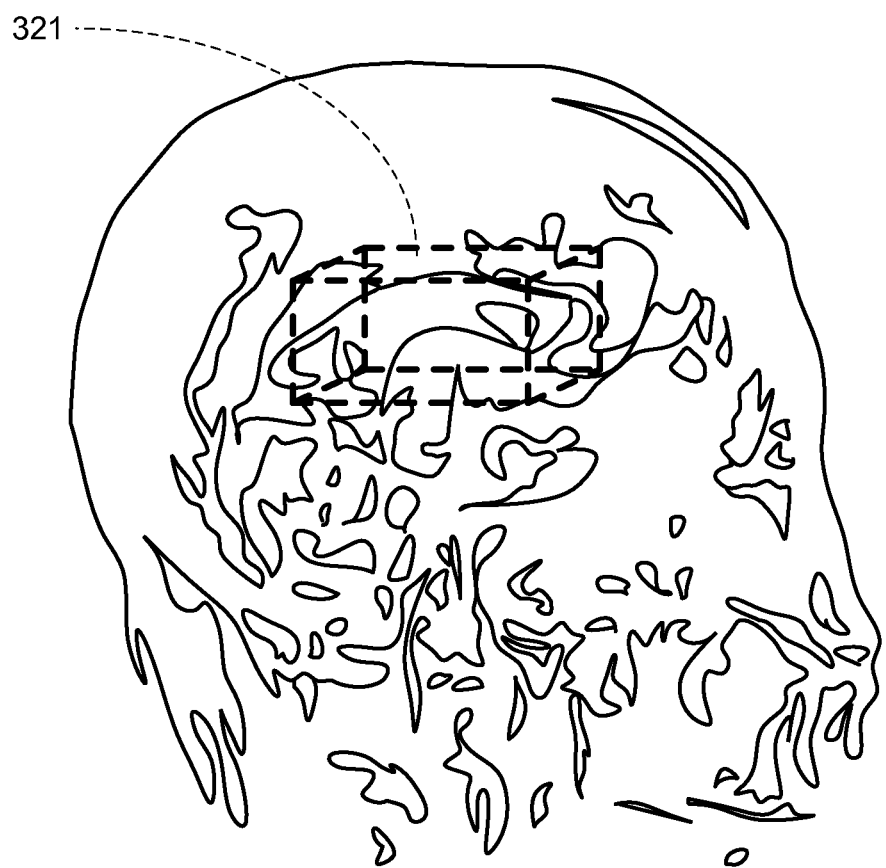
FIG. 5 is the pre-processing region of interest in a region of interest initialization phase of operation.

Referring now to FIG. 5, therein is shown the pre-processing region of interest 321 in a region of interest initialization phase of operation. In the interests of clarity and illustration, the pre-processing region of interest 321 is shown as a dotted rectangular volume, but it is understood that the region of interest can be any shape or size smaller than the size of the anatomical structures which have been isolated from the pre-operation non-invasive imaging volume 208 of FIG. 2. Rigid registered feature points can also be determined in the pre-processing region of interest 321.

Figure 6:
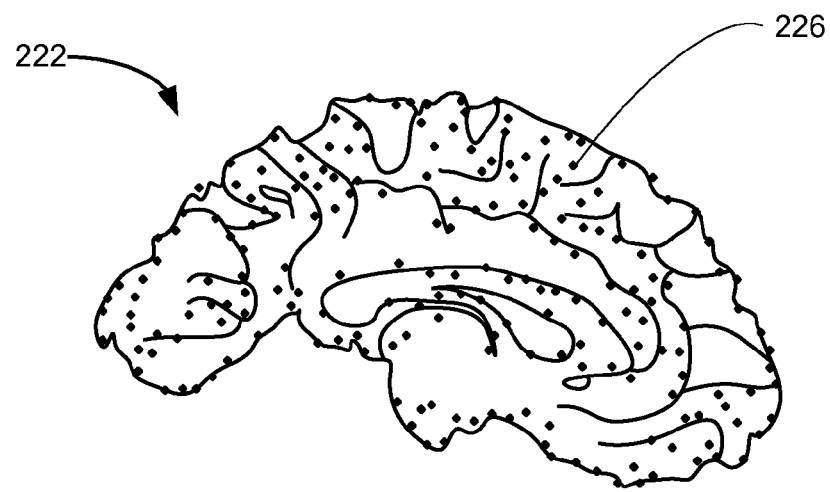
FIG. 6 is an example of the feature points in a feature point generation phase of operation.

Referring now to FIG. 6, therein is shown an example of the feature points 226 in a feature point generation phase of operation. The feature points 226 are shown overlaid on the region of interest 222 as dots on or near features of the region of interest 222. For illustrative purposes, the features of the region of interest 222 have been simplified, but it is understood that ordinarily the feature points 226 will closely track features of the region of interest 222. In this example, a portion of a cross-sectional view of the brain is shown, but it is understood that the region of interest 222 can be larger or smaller as necessitated by surgical requirements. It is also understood that this view is for example only, and that the feature points 226 can be part of a three-dimensional point cloud.

Figure 7:
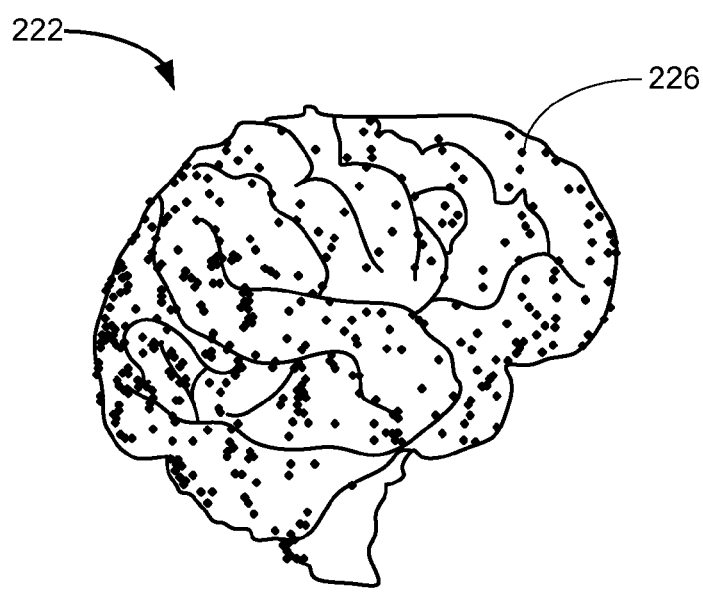
FIG. 7 is an example of the feature points in a further feature point generation phase of operation.

Referring now to FIG. 7, therein is shown an example of the feature points 226 in a further feature point generation phase of operation. In this example, an external three-dimensional view of the region of interest 222 can be seen. The feature points 226 are overlaid on the region of interest 222. As with FIG. 6, features of the region of interest 222 have been simplified for clarity when viewing the figure, and it is understood that ordinarily the feature points 226 can closely track features of the region of interest 222.

Figure 8:
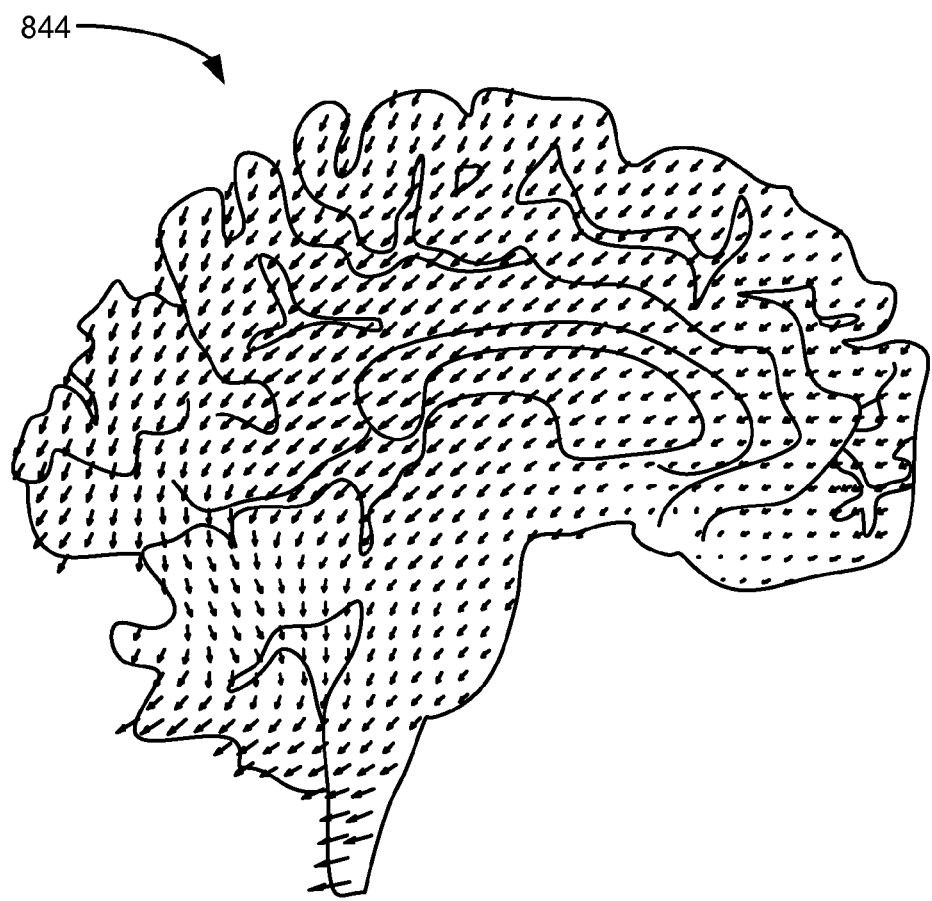
FIG. 8 is a displacement field in a volume reconstruction phase of operation.

Referring now to FIG. 8, therein is shown a displacement field 844 in a volume reconstruction phase of operation. In this example, the displacement field 844 is shown as a field of arrows of varying lengths. After the matched point cloud is determined, the displacement field 844 can be generated based on the difference in position between the feature points 226 of FIG. 2 and the corresponding points determined in rigid registration. The varying lengths of the arrows shown represent the magnitude of displacement between the feature points 226 and the corresponding points. The displacement field 844 can show how the structure of interest 212 of FIG. 2 may deform. Using the displacement field 844, surgeons can more accurately predict where locations of interest (again, such as tumors or hemorrhaging locations, for example) will be even after the process of surgery has deformed the surrounding tissue or organs.

Figure 9:
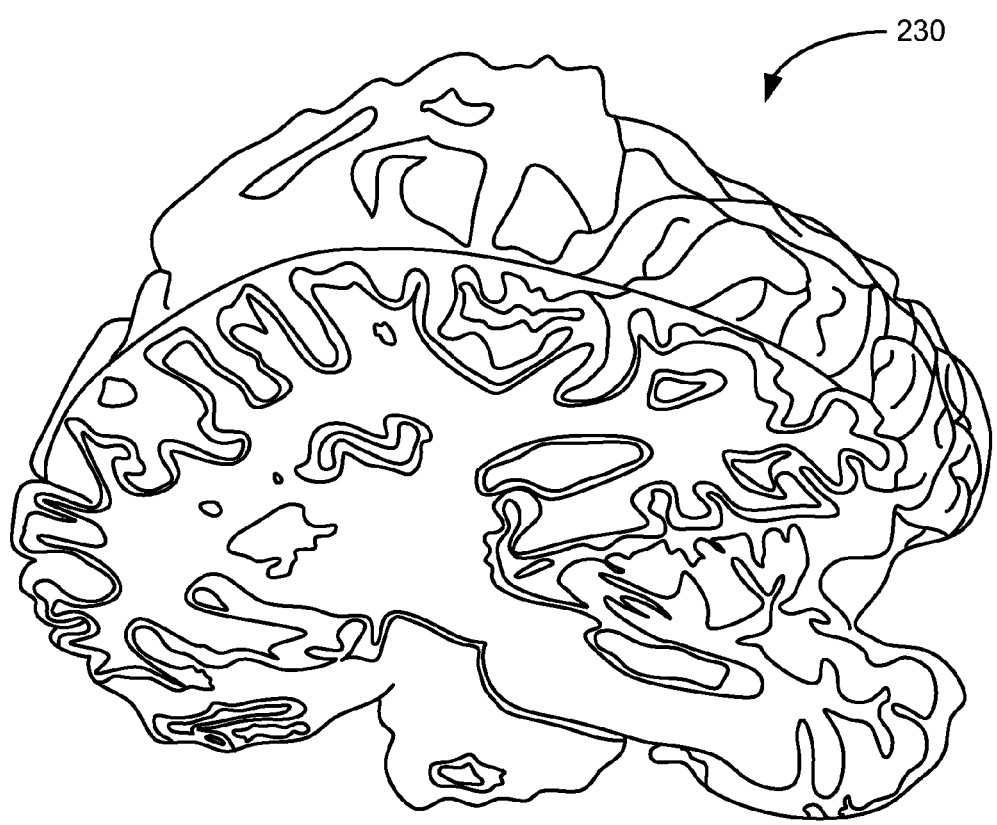
FIG. 9 is a three-dimensional cross-sectional view of the non-rigid registered volume in a final registration phase of operation.

Referring now to FIG. 9, therein is shown a three-dimensional cross-sectional view of the non-rigid registered volume 230 in a final registration phase of operation. The non-rigid registered volume 230 in this example is the brain, and for illustrative purposes, a cutaway view is shown so that internal and external features are visible. Once non-rigid registration has been completed after being initialized with results from rigid registration, it has been found that accurate registration of features both internal and external to the non-rigid registered volume 230 is possible. The non-rigid registered volume along with the displacement field 844 of FIG. 8 can be used to accurately and safely plan further stages of the image-guided surgery.

Figure 10:
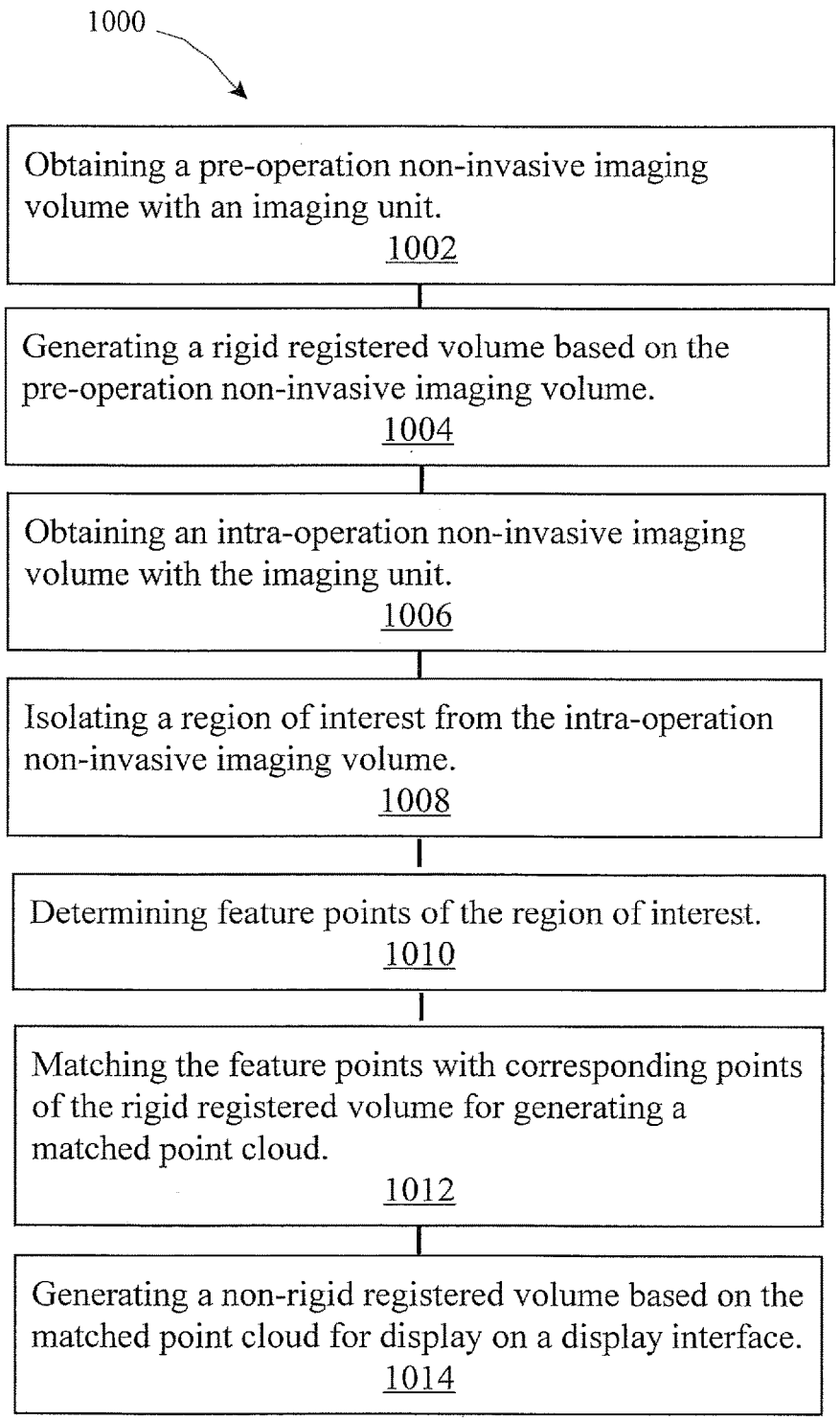
FIG. 10 is a flow chart of a method of operation of an image registration system in a further embodiment of the present invention.

Referring now to FIG. 10, therein is shown a flow chart of a method 1000 of operation of an image registration system in a further embodiment of the present invention. The method 1000 includes: obtaining a pre-operation non-invasive imaging volume with an imaging unit in a block 1002; generating a rigid registered volume based on the pre-operation non-invasive imaging volume in a block 1004; obtaining an intra-operation non-invasive imaging volume with the imaging unit in a block 1006; isolating a region of interest from the intra-operation non-invasive imaging volume in a block 1008; determining feature points of the region of interest in a block 1010; matching the feature points with corresponding points of the rigid registered volume for generating a matched point cloud in a block 1012; and generating a non-rigid registered volume based on the matched point cloud for display on a display interface in a block 1014.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization.

Another important aspect of the present invention is that it valuably supports and services the historical trend of reducing costs, simplifying systems, and increasing performance.

These and other valuable aspects of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hitherto set forth herein or shown in the accompanying drawings are to be interpreted in an illustrative and non-limiting sense.

What is claimed is:

1. A method of operation of an image registration system comprising:
    obtaining a pre-operation non-invasive imaging volume with an imaging unit;
    generating a volume image based on the pre-operation non-invasive imaging volume;
    obtaining an intra-operation non-invasive imaging volume with the imaging unit;
    isolating a region of interest from the intra-operation non-invasive imaging volume;
    determining feature points of the region of interest;
    matching the feature points with corresponding points of the volume image for generating a matched point cloud;
    generating a non-rigid registered volume based on the matched point cloud for display on a display interface, wherein a type of pre-operation non-invasive imaging volume and a type of intra-operation non-invasive imaging volume are tailored to a type of image-guided surgery performed, wherein generating the non-rigid registered volume includes using the matched point cloud as an input to a radial basis function to reconstruct volume data, wherein matching the feature points with the corresponding points of the volume image includes:
    using the volume image as a reference map for matching the region of interest to anatomical features of the volume image;
    determining a maximum displacement distance between the feature points and the corresponding points; and
    restricting a search space for the corresponding points to be within the maximum displacement distance from the feature points.

2. The method as claimed in claim 1 further comprising:
    isolating the anatomical structures from the pre-operation non-invasive imaging volume; and
    generating the volume image based on the anatomical structures.

3. The method as claimed in claim 1 further comprising:
    isolating a structure of interest from the intra-operation non-invasive imaging volume; and
    isolating the region of interest from the structure of interest.

4. The method as claimed in claim 1 further comprising isolating a structure of interest using the anatomical structures as a reference guide.

5. A method of operation of an image registration system comprising:
    obtaining a pre-operation non-invasive imaging volume with an imaging unit;
    isolating anatomical structures from the pre-operation non-invasive imaging volume;
    generating a rigid registered volume based on the anatomical structures;
    obtaining an intra-operation non-invasive imaging volume with the imaging unit;
    isolating a structure of interest from the intra-operation non-invasive imaging volume using the anatomical structures as a reference guide;
    isolating a region of interest from the structure of interest;
    determining feature points of the region of interest;
    matching the feature points with corresponding points of the rigid registered volume for generating a matched point cloud including:
    using the rigid registered volume as a reference map for matching the region of interest to the anatomical features of the rigid registered volume,
    determining a maximum displacement distance between the feature points and the corresponding points, and
    restricting a search space for the corresponding points to be within the maximum displacement distance from the feature points; and
    generating a non-rigid registered volume based on the matched point cloud for display on a display interface, wherein a type of pre-operation non-invasive imaging volume and a type of intra-operation non-invasive imaging volume are tailored to a type of image-guided surgery performed, wherein generating the non-rigid registered volume includes using the matched point cloud as an input to a radial basis function to reconstruct volume data.

6. The method as claimed in claim 5 further comprising selecting a pre-processing region of interest of the anatomical structures of the pre-operation non-invasive imaging volume.

7. The method as claimed in claim 5 further comprising smoothing the anatomical structures.

8. The method as claimed in claim 5 wherein generating the rigid registered volume includes running a surface-fitting algorithm on the anatomical structures.

9. The method as claimed in claim 5 further comprising validating the accuracy of the rigid registered volume by comparing the rigid registered volume to the pre-operation non-invasive imaging volume.

10. An image registration system
    for obtaining a pre-operation non-invasive imaging volume and for obtaining an intra-operation non-invasive imaging volume comprising:
    a memory for storing an application, the application configured for:
        generating a rigid registered volume based on the pre-operation non-invasive imaging volume,
        isolating a region of interest from the intra-operation non-invasive imaging volume,
        determining feature points of the region of interest,
        matching the feature points with corresponding points of the rigid registered volume for generating a matched point cloud, and
        generating a non-rigid registered volume based on the matched point cloud for display on a display interface, wherein a type of pre-operation non-invasive imaging volume and a type of intra-operation non-invasive imaging volume are tailored to a type of image-guided surgery performed, wherein generating the non-rigid registered volume includes using the matched point cloud as an input to a radial basis function to reconstruct volume data, wherein matching the feature points with the corresponding points of the volume image includes:
    using the volume image as a reference map for matching the region of interest to anatomical features of the volume image;
    determining a maximum displacement distance between the feature points and the corresponding points; and
    restricting a search space for the corresponding points to be within the maximum displacement distance from the feature points; and
    a processor for processing the application.

11. The system as claimed in claim 10
wherein the application is further configured for isolating the anatomical structures from the pre-operation non-invasive imaging volume; and
wherein the application is further configured for generating the rigid registered volume based on the anatomical structures.

12. The system as claimed in claim 10
wherein the application is further configured for isolating a structure of interest from the intra-operation non-invasive imaging volume; and
wherein the application is further configured for isolating the region of interest from the structure of interest.

13. The system as claimed in claim 10
wherein the application is further configured for isolating anatomical structures from the pre-operation non-invasive imaging volume; and
wherein the application is further configured for isolating a structure of interest using the anatomical structures as a reference guide.

14. The system as claimed in claim 10
wherein the application is further configured for isolating anatomical structures from the pre-operation non-invasive imaging volume; and
wherein the application is further configured for isolating a structure of interest using the anatomical structures as a reference guide; and
wherein the application is further configured for isolating the region of interest from the structure of interest; and
wherein the application is further configured for matching the feature points including:
using the rigid registered volume as a reference map for matching the region of interest to the anatomical features of the rigid registered volume;
determining a maximum displacement distance between the feature points and the corresponding points; and
restricting a search space for the corresponding points to be within the maximum displacement distance from the feature points.

15. The system as claimed in claim 14 wherein the application is further configured for selecting a pre-processing region of interest of the anatomical structures of the pre-operation non-invasive imaging volume.

16. The system as claimed in claim 14 wherein the application is further configured for smoothing the anatomical structures.

17. The system as claimed in claim 14 wherein the application is further configured for running a surface-fitting algorithm on the anatomical structures.

18. The system as claimed in claim 14 wherein the application is further configured for validating the accuracy of the rigid registered volume by comparing the rigid registered volume to the pre-operation non-invasive imaging volume.

* * * * *